(12) United States Patent
Sano

(10) Patent No.: US 7,323,007 B2
(45) Date of Patent: Jan. 29, 2008

(54) SOFT STENT WITH EXCELLENT FOLLOW-UP CAPABILITY TO BLOOD VESSEL

(75) Inventor: Yoshihiko Sano, Osaka (JP)

(73) Assignee: Nipro Corporation, Osaka-shi, Osaka (JP)

( * ) Notice: Subject to any disclaimer, the term of this patent is extended or adjusted under 35 U.S.C. 154(b) by 110 days.

(21) Appl. No.: 10/559,124

(22) PCT Filed: May 27, 2004

(86) PCT No.: PCT/JP2004/007256

§ 371 (c)(1),
(2), (4) Date: Dec. 1, 2005

(87) PCT Pub. No.: WO2004/108201

PCT Pub. Date: Dec. 16, 2004

(65) Prior Publication Data

US 2006/0142843 A1    Jun. 29, 2006

(30) Foreign Application Priority Data

Jun. 2, 2003   (JP)   ............................. 2003-156431
Jun. 5, 2003   (JP)   ............................. 2003-160487
Jul. 8, 2003   (JP)   ............................. 2003-271708

(51) Int. Cl.
*A61F 2/06*   (2006.01)

(52) U.S. Cl. .................................................. 623/1.15

(58) Field of Classification Search ....... 623/1.11–1.23
See application file for complete search history.

(56) References Cited

U.S. PATENT DOCUMENTS 4,733,665 A    3/1988   Palmaz
6,033,433 A *  3/2000   Ehr et al. ................... 623/1.16
6,123,721 A    9/2000   Jang
6,325,821 B1 * 12/2001  Gaschino et al. ........... 623/1.15
6,749,629 B1 *  6/2004  Hong et al. ................. 623/1.15
6,790,227 B2 *  9/2004  Burgermeister ............. 623/1.15

(Continued)

FOREIGN PATENT DOCUMENTS

JP    6-181993 A    7/1994

(Continued)

*Primary Examiner*—Suzette Gherbi
(74) *Attorney, Agent, or Firm*—Birch, Stewart, Kolasch & Birch, LLP

(57) ABSTRACT

To provide a lumen-friendly, flexible stent which is excellent in trackability to lumens (thus, it is able to pass through the three-dimensionally meandering lumens), substantially free from shortening (shortening of the length), uniformly expandable.

A stent according to the present invention comprises radially expandable annular members (1) which are aligned in a longitudinal direction of the stent, and one or more coupling elements (2) that couple adjoining two annular members (1) in the longitudinal direction of the stent, wherein said annular member comprises first annular member elements (11) and second annular member elements (12), which have a plane symmetrical pattern and are alternately connected in the circumferential direction of the annular member, and wherein under the condition that the stent is unfolded onto a plane, the first annular member element (11) includes one wave mountain, while the second annular member element (12) includes one wave trough, the adjoining two annular members being connected between the junctions which connect the first annular member elements (11) and second annular member elements (12) of the respective annular members.

10 Claims, 14 Drawing Sheets

U.S. PATENT DOCUMENTS

| | | | |
|---|---|---|---|
| 6,835,203 B1 * | 12/2004 | Vardi et al. | 623/1.34 |
| 6,955,686 B2 * | 10/2005 | Majercak et al. | 623/1.15 |
| 7,004,968 B2 * | 2/2006 | Lootz et al. | 623/1.15 |
| 2002/0045933 A1 * | 4/2002 | Jang | 623/1.15 |
| 2002/0058988 A1 | 5/2002 | Fischell et al. | |
| 2003/0055489 A1 * | 3/2003 | Kveen et al. | 623/1.15 |
| 2003/0149469 A1 | 8/2003 | Wolinsky et al. | |
| 2004/0167608 A1 * | 8/2004 | Cheng | 623/1.15 |

FOREIGN PATENT DOCUMENTS

| | | |
|---|---|---|
| JP | 8-155035 A | 6/1996 |
| JP | 2002-102385 A | 4/2002 |
| JP | 2002/541910 A | 12/2002 |
| WO | WO-96/03092 A1 | 2/1996 |
| WO | WO-96/26689 A1 | 9/1996 |
| WO | WO-99/40876 A2 | 8/1999 |
| WO | WO-00/62710 A1 | 10/2000 |
| WO | WO-02/24111 A2 | 3/2002 |
| WO | WO-02/26163 A2 | 4/2002 |

* cited by examiner

Fig. 5
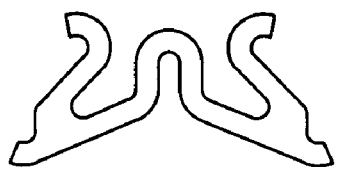
Fig. 5A
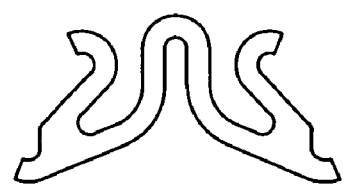
Fig. 5B
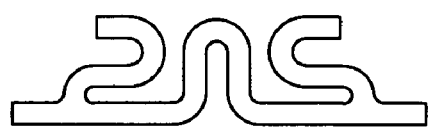
Fig. 5C
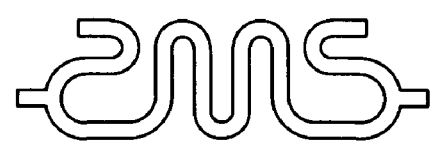
Fig. 5D

SOFT STENT WITH EXCELLENT FOLLOW-UP CAPABILITY TO BLOOD VESSEL

TECHNICAL FIELD

The present invention relates to a stent that is implanted in a human body to maintain a diameter of a body lumen such as blood vessels.

BACKGROUND ART

So far, stents have been used to expand a diameter of the body lumen such as the blood vessel and keep it to the expanded luminal diameter. The stent may be expanded by various methods such as balloon dilation, self-expansion using a shape memory material, mechanical expansion, or the like. The most widely used method is the balloon dilation. In the balloon dilation, a stent is introduced into a desired site in the body together with a balloon catheter, expanded by inflation of balloon to dilate a diameter of the lumen, and retained at the dilated site even after removing the deflated balloon from the site. The stent generally comprises luminal diameter-holding portions for dilating and holding the diameter of the lumen such as blood vessel, and joint portions for connecting the luminal diameter-holding portions in the longitudinal direction of the stent, and the stent is adapted to keep its expanded shape after expansion.

Proposed stents comprising luminal diameter-holding portions and joint portions include, for example, a stent comprising plural cylindrical components which are separately expandable in the radial direction thereof and are connected to one another so as to align on a common axis (Patent document 1); a stent comprising a tubular member expandable in the radial direction, the tubular member being constituted by a plurality of elongated members intersecting with one another (Patent document 2); a stent comprising at least two unitary wire-like circular members each bent to form a plurality of substantially straight, non-overlapping segments connected at axial bends; the at least two circular members having at least one pair of aligned axial bends; and the at least two circular members connected by at least one substantially rigid joint at least one pair of aligned axial bends (Patent document 3); a stent formed of a tube having a patterned shape which has first and second meander patterns having axes extending in first and second directions (Patent document 4); and a stent of an open structure type comprising a plurality of open cylindrical segments, each segment being defined by an interconnected struts, the segment being interconnected at end portions thereof by a plurality of diagonal interconnecting elements (Patent document 5).

These stents have been improved to some extent, but they still put a load on the lumen such as the blood vessel in the vicinity of edges of the expanded stent, resulting in obstruction or stenosis of the lumen. Further, it can not be said that these stents have sufficient flexibility, and thus it is often difficult to introduce the stent into the objective site if the lumen has a three-dimensionally meandering course. In addition, the stents may cause wounds in the blood vessel during insertion into the objective site. If there is a branched blood vessel at the inflated position, it is hardly difficult to form a lateral hole in the placed stent.

| Patent document 1: | JP H06-181993A |
|---|---|
| Patent document 2: | JP S62-231657A |
| Patent document 3: | JP H08-155035A |
| Patent document 4: | JP H10-503676A |
| Patent document 5: | JP H11-505441A |

DISCLOSURE OF INVENTION

Problems to be Solved by the Invention

In view of the above circumstances, the present invention has been made to provide a flexible stent which is excellent in trackability to lumens (thus, it is able to pass through the three-dimensionally meandering lumens), substantially free from shortening (shortening of the length), uniformly expandable, and lumen-friendly.

Means for Solving the Problems

A stent according to the present invention comprises radially expandable annular members which are aligned in a longitudinal direction of the stent, and one or more coupling elements that couple adjoining two annular members in the longitudinal direction of the stent, wherein said annular member comprises first annular member elements and second annular member elements, which have a plane symmetrical pattern and are alternately connected in the circumferential direction of the annular member, and wherein, under the condition that the stent is unfolded onto a plane, said first annular member element includes one wave mountain, while said second annular member element includes one wave trough, the adjoining two annular members being connected between the respective junctions which connect the first annular member elements and second annular member elements of the respective annular members.

Here, the first annular member element and second annular member element may be connected directly with each other in the circumferential direction of the annular member or they may be connected with the connecting segments in the circumferential direction of the annular member. The first and second annular member elements may take any pattern without being limited to specific patterns, provided that the first and second annular member elements are of a waveform having loops with different lengths on both sides thereof and that they, when folded on a plane, can be alternately connected in the vertical direction of the stent. As the first and second annular member elements, there may be used various shaped elements, for example, elements of an approximately sinusoidal wave pattern, elements composed of parallel two linear segments with different lengths that are connected by an arched segment and the like. Under the condition that the stent is unfolded onto a plane, the first and second annular member elements may be oriented toward the same direction which is inclined to the longitudinal axis of the stent, or may be oriented toward the direction parallel to the longitudinal axis of the stent. The adjoining two annular members are preferably connected between junctions located at the closest positions, among the junctions between the connecting segments and the first annular member elements or second annular member elements of the respective annular members. Further, under the condition that the stent is unfolded onto a plane, the vertical directions of the adjoining annular members are oriented toward the same direction.

In the present invention, the term "mountain" means a section of the wave that is convex toward the distal end of the stent (or concave toward the proximal end of the stent), while the term "trough" means a section of the wave that is concave toward the distal end of the stent (or convex toward the proximal end of the stent). For convenience sake, the right end of the drawing is set as the distal end of the stent and thus the wave mountain is a wave that is convex rightward, while the wave trough is a wave that is convex leftward.

As a material for the stent, there may be used stainless steels, tungsten, tantalum, nickel-titanium alloys and the like.

When the first annular member elements and second annular member elements are oriented toward the directions parallel with the longitudinal axis of the stent, under the condition that the stent is unfolded onto a plane, they have such a construction that the first annular member element includes a relatively long upper linear segment and a relatively short lower linear segment, which are in parallel with the longitudinal axis of the stent, the upper linear segment and lower linear segment being connected with an arched segment that is convex rightward, while the second annular member element includes a relatively long upper linear segment and a relatively short lower linear segment, which are in parallel with the longitudinal axis of the stent, the upper linear segment and lower linear segment being connected with an arched segment that is convex leftward. The first annular member element and second annular member element are joined together at the upper linear segment of one annular member element and the lower linear segment of the other annular member element. In the above construction, the adjoining two annular members are preferably joined together at the junctions with a pattern which is convex toward the annular member to be connected, among the junctions between the respective connecting segments and the upper linear segment or lower linear segment of the annular member element.

Preferably, the adjoining two annular members are out of phase with each other so that the first annular member elements and the second annular member elements of the respective annular members are opposed to each other on the same longitudinal lines. Further, the pattern of the coupling element may be a linear pattern (provided that they can be connected with a straight line) or a curved pattern. If the coupling element is of a curved pattern, the pattern of the curved line is preferably of S-shaped, inverted S-shaped or a waveform. If the curved pattern is a waveform, the curved line may be a curved pattern with one wave mountain or a curved pattern with plural wave mountains.

Effects of the Invention

According to the present invention, the stent has potential for providing the following effects: (1) the whole stent is flexible to bending and thus excellent in trackability to lumens since the annular members that form a tubular wall of the stent are composed of repeated snaky patterns of an annular member element (i.e., a unit pattern); (2) the stent is hard to produce shortening since the adjoining two annular members are connected between junctions where the first annular member elements and second annular member elements of the respective annular members are connected, in a manner, at the middle positions of wavelike patterns with the coupling elements; (3) the stent is excellent in radial expandability, easy to provide a lateral hole since the annular members that form a tubular wall of the stent are composed of repeated circumferentially continuing wavy patterns. Also, the stent is excellent in balance at the time of expansion since the stent expands uniformly along the entire length of the stent.

BRIEF DESCRIPTION OF DRAWINGS

FIG. 5 is a view illustrating embodiments of a coupling element of the present invention under the condition of connection;

EXPLANATION OF REFERENCE SIGN

Figure 1:
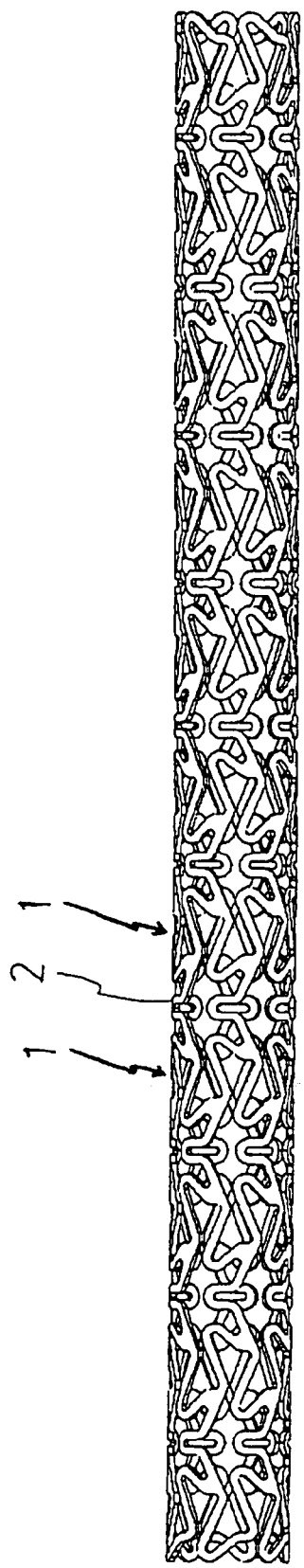
FIG. 1 is an enlarged plan view of a stent according to one embodiment of the present invention.

1: annular member
11: first annular member element
111: upper linear segment
112: lower linear segment
113: arched segment that is convex rightward
12: second annular member element
121: upper linear segment
122: lower linear segment
123: arched segment that is convex leftward
13: junction of a first annular member element with a second annular member element located just below the same
14: junction of a first annular member element with a second annular member element located just above the same
15: connecting segment
16: junction of the connecting segment with the second annular member element located just below the same
17: junction of the connecting segment with the first annular member element located just below the same
18: junction of the connecting segment with the upper linear segment of the second annular member
19: junction of the connecting segment with the upper linear segment of the first annular member
2: coupling element Best Mode for Carrying Out the Invention In the stent, the first annular member element includes a relatively long upper linear segment and a relatively short lower linear segment which are parallel to the longitudinal axis of the stent, said upper linear segment and lower linear segment being connected with an arched segment that is convex rightward, while the second annular member element includes a relatively long upper linear segment and a relatively short lower linear segment which are parallel to the longitudinal axis of the stent, the upper linear segment and lower linear segment being connected by an arched segment that is convex leftward. The first annular member element and second annular member element are joined between the upper linear segment of one annular member element and the lower linear segment of the other annular member element. The adjoining two annular members are out of phase with each other so that the first annular member elements and the second annular member elements of the respective annular members are located opposite each other on the same axes. The adjoining two annular members are connected between the junctions with a pattern which is convex toward the annular member to be connected among the junctions which connect the connecting segment and the upper linear segment or lower linear segment of the respective annular members.

EMBODIMENT

Embodiment 1

Figure 2:
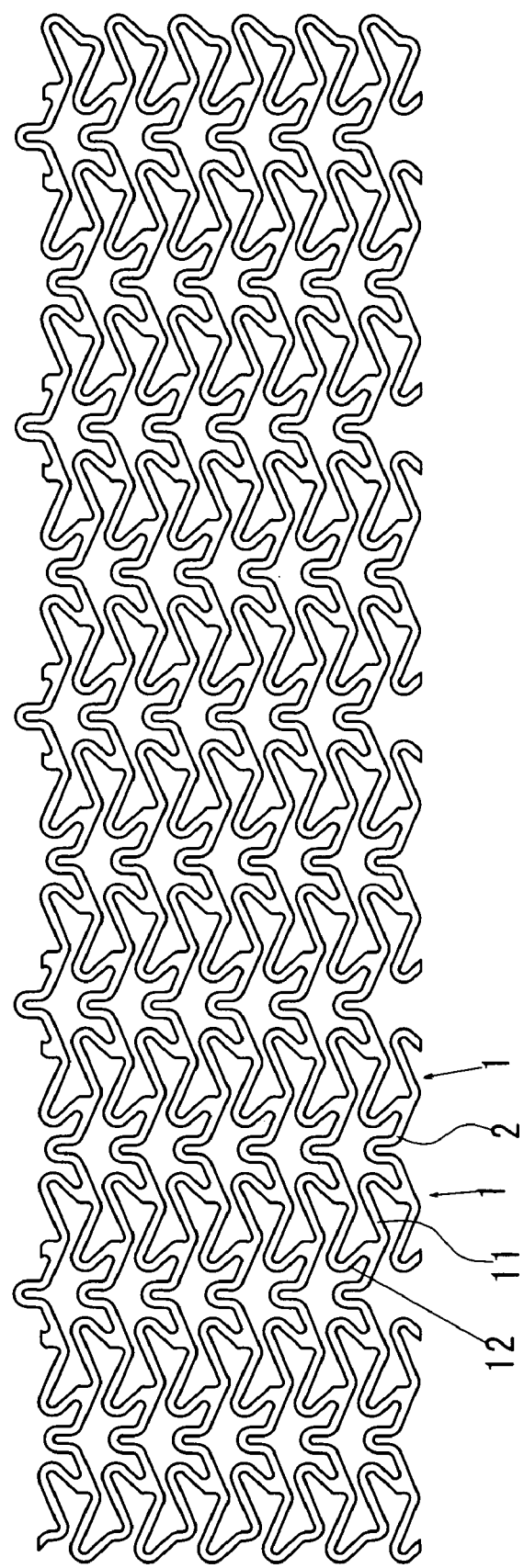
FIG. 2 is a development of the stent shown in FIG. 1.
Figure 3:
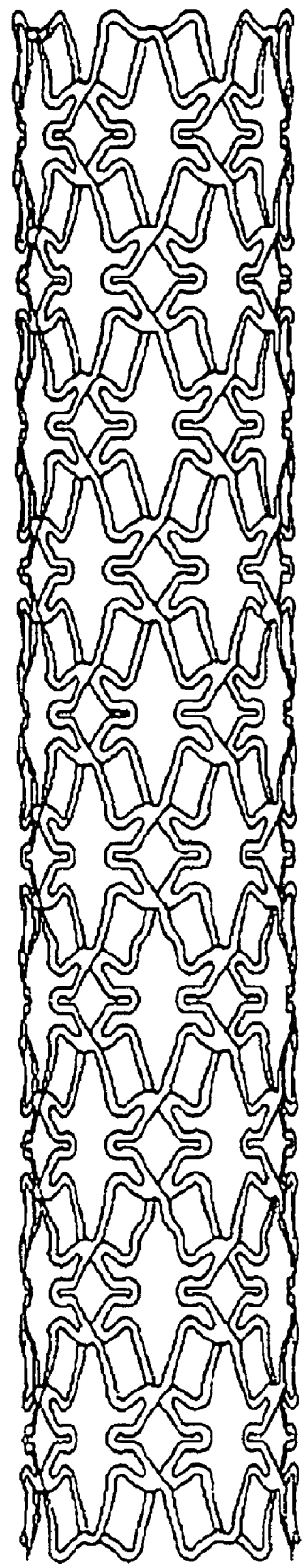
FIG. 3 is an enlarged plan view illustrating an expanded state of the stent shown in FIG. 1.
Figure 4:
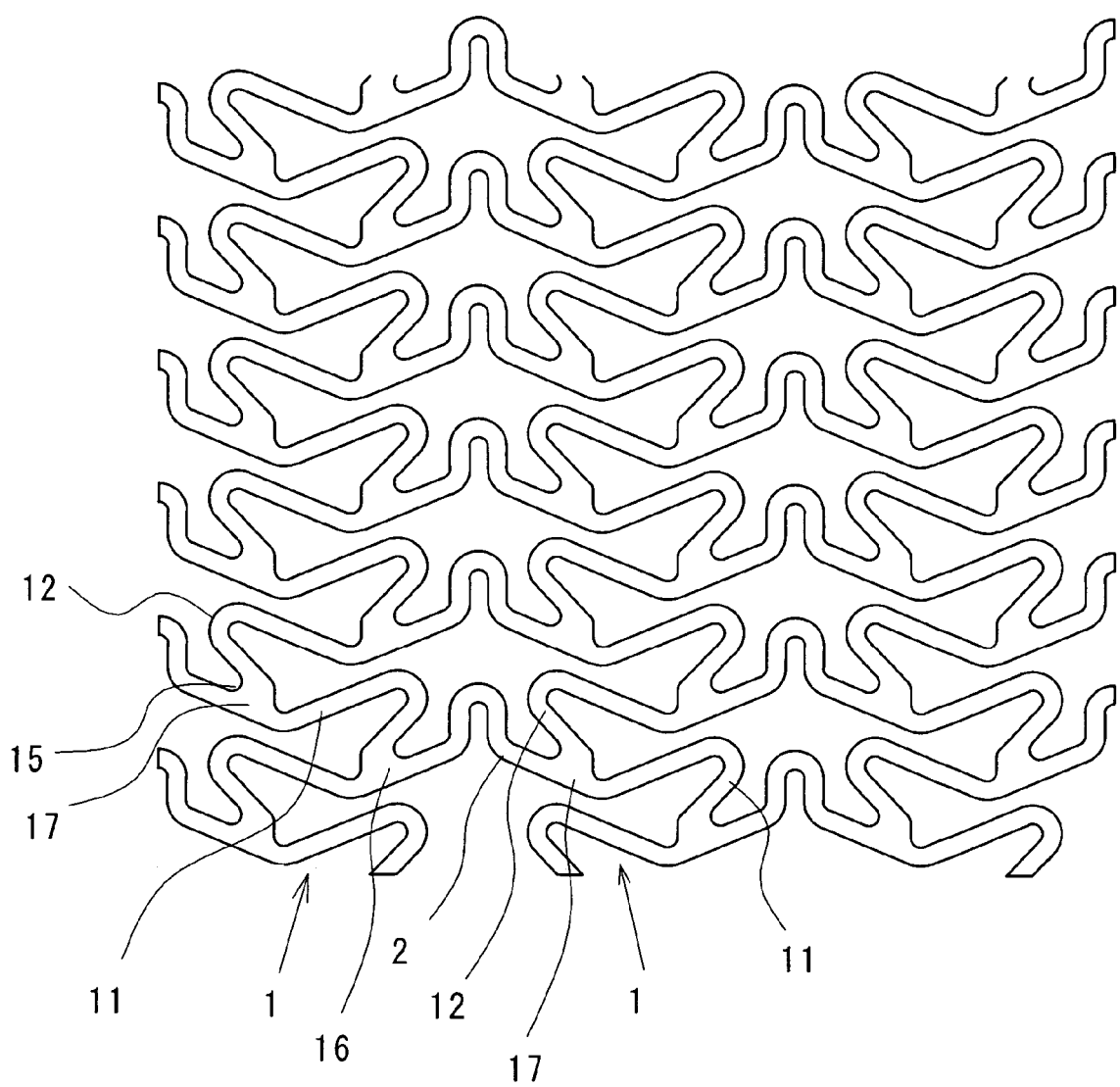
FIG. 4 is a partially enlarged view of FIG. 2.

FIG. 1 is an enlarged plan view of a stent according to embodiment 1 of the present invention, FIG. 2 is a development of the stent shown in FIG. 1, FIG. 3 is an enlarged plan view illustrating an expanded state of the stent shown in FIG. 1, and FIG. 4 is a partially enlarged view of FIG. 2.

As shown in FIGS. 1 to 3, the stent of embodiment 1 comprises eleven annular members 1 which are radially expandable and arranged in the longitudinal direction of the stent. The adjoining annular members 1, 1 are longitudinally connected with six coupling elements 2 of a pattern as shown in FIG. 5A. Each annular member 1 comprises first annular member elements 11 and second annular member elements 12, which have plane symmetrical patterns and are alternately connected in the circumferential direction by a connecting segment 15. Under the condition that the stent is unfolded onto a plane, the first annular member element 11 has a wave mountain (a wave which is convex rightward), while the second annular member element 12 has a wave trough (a wave which is convex leftward). The adjoining two annular members 1, 1 are out of phase with each other so that the first annular member elements 11 and the second annular member elements 12 of the respective annular members are opposed to each other on the same longitudinal lines. As shown in FIG. 4, the adjoining two annular members 1, 1 are coupled between a junction 17 which connects the connecting segment 15 and the first annular member element 11 and a junction 16 which connects the connecting segment 15 and the second annular member element 12.

The annular member 1 is a radially expandable member for holding a body lumen open and is composed of the first annular member elements 11 and the second annular member elements 12, which have a plane symmetrical pattern and are alternately connected in the circumferential direction with the connecting segment 15. Under the condition that the stent is unfolded onto a plane, the first annular member element 11 and second annular member element 12 are respectively composed of a wave mountain protruded upper-right and a wave trough protruded upper-left. The connecting segment 15 that connects the adjoining upper and lower first annular member element 11 and second annular member element 12 is connected to the second annular member element 12 at the junction 16 when the first annular member element 11 is located above the second annular member element 12. When the first annular member element 11 is located below the second annular member element 12, the connecting segment 15 is connected to the first annular member element 11 at the junction 17. The first and second annular member elements 11, 12 may take any desired pattern without being limited to a specific pattern, provided that they have vertically and alternately connectable patterns under the condition that the stent is unfolded onto a plane, i.e., they are of a waveform. Preferably, the adjoining two annular members 1, 1, when folded on a plane, have directions which are the same in the vertical direction.

The adjoining two annular members 1, 1 are coupled between closely-spaced junctions, among the junctions 17, 16 between the respective connecting segment 15 and the first annular member element 11 or the second annular member element 12. More particularly, if the adjoining annular members 1, 1 are oriented toward the same vertical direction as illustrated in FIG. 4, the adjoining two annular members 1, 1 are coupled between the junction 16 which connects the connecting segment 15 of the right annular member 1 and second annular member element 12 located below the same, and the junction 17 which connects the connecting segment 15 of the left annular member 1 and second annular member element 11 located below the same. On the other hand, if the adjoining annular members 1, 1 are oriented toward the opposite vertical direction, the connection between the junctions 16, 16 and the connection between the junctions 17, 17 are alternately repeated.

The annular members that constitute a tubular wall of the above stent are composed of repeated wavelike patterns, so that the whole stent is flexible enough to respond to the bending, and thus excellent in trackability to lumens. Further, the adjoining two annular members are coupled between the respective junctions which connect the first annular member elements and the second annular member elements, i.e., between the middle portions of the wavelike patterns with the coupling elements, the stent hardly produces shortening of the length. Further, the annular members that constitute a tubular wall of the stent are composed of repetition of circumferentially continuing wavelike patterns, and thus the stent is high in radial expandability and makes it easy to provide a lateral hole. In addition, the stent uniformly expands along the entire length thereof, so that it shows excellent structural balance at the time of expansion.

Embodiment 2

Figure 6:
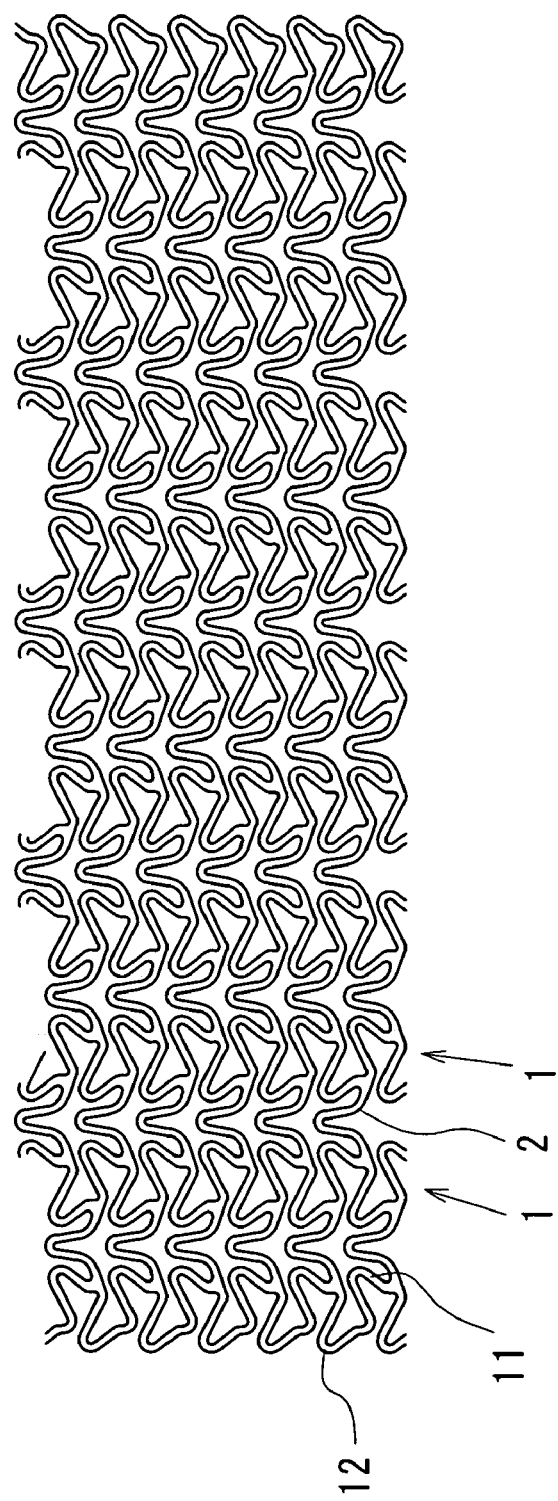
FIG. 6 is a development of a stent according to another embodiment of the present invention.

Embodiment 2 of the present invention will be demonstrated below, making reference to FIG. 6.

The stent of embodiment 2 is a modification of the stent of embodiment 1, wherein the coupling elements are formed into a pattern as illustrated in FIG. 5B. As illustrated in FIG. 6, the stent comprises eleven annular members 1 and the adjoining two annular members 1, 1 are coupled with six coupling elements 2 of a pattern shown in FIG. 5B. The adjoining two annular members 1, 1 are coupled between the junctions 16 of the right annular member 1 and the junctions 17 of the left annular member 1 with the coupling elements 2.

The stent of this embodiment is superior to that of embodiment 1 in flexibility for bending, and thus it is excellent in trackability to lumens. Further, the stent hardly produces shortening of the length and is high in radial expandability. In addition, the stent makes it easy to provide a lateral hole and shows good structural balance at the time of expansion.

Embodiment 3

Figure 7:
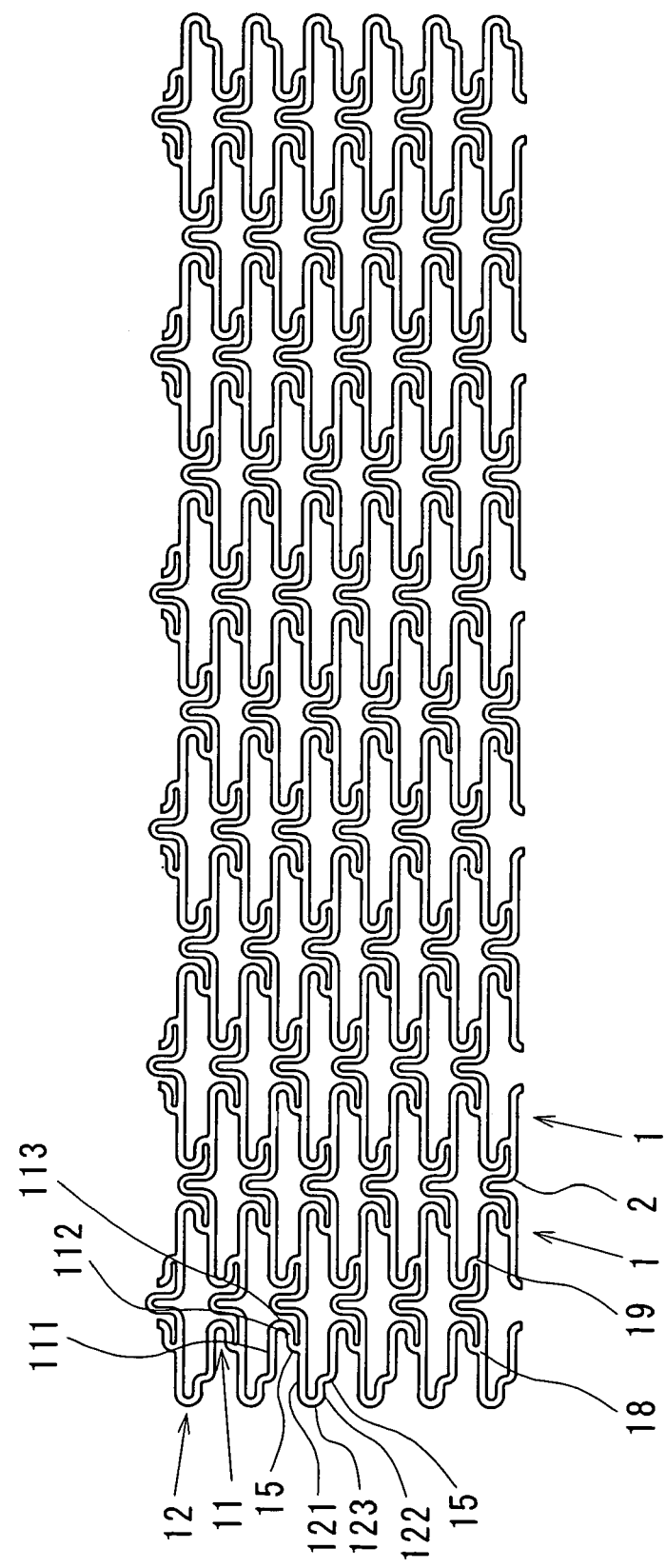
FIG. 7 is a development of a stent according to another embodiment of the present invention.

Embodiment 3 of the present invention will be demonstrated below, making reference to FIG. 7.

The stent of embodiment 3 is a modification of the stent of embodiment 1, in which first annular member elements 11 and second annular member elements 12 are aligned parallel with the longitudinal axis of the stent. The stent includes twelve annular members 1 and coupling elements 2 formed into a pattern as illustrated in FIG. 5C. As illustrated in FIG. 7, the stent comprises twelve annular members 1 which are radially expandable and are arranged in the longitudinal direction of the stent. The adjoining two annular members 1, 1 are longitudinally connected with six coupling elements 2 of a pattern shown in FIG. 5C.

The annular member 1 includes pairs of relatively long upper linear segments 111, 121 and relatively short lower linear segments 112, 122, which are parallel with the longitudinal axis of the stent. The upper linear segment 111, 121 of one pair is respectively connected to the lower linear segment 122, 112 of the other pair. The adjoining two annular members 1, 1 are coupled between junctions 19 which connect the connecting segment 15 and the upper linear segments 111 of the first annular member element 11 in the right annular member 1 and junctions 18 which connect the connecting segment 15 and the upper linear segments 121 of the second annular member element 12 in the left annular member 1.

Under the condition that the stent is unfolded onto a plane, the first annular member element 11 includes longitudinally parallel, relatively long upper linear segment 111 and relatively short lower linear segment 112 in pair, and the upper linear segment 111 and lower linear segment 112 are connected with an arched segment 113 which is convex rightward, while the second annular member element 12 includes longitudinally parallel, relatively long upper linear segment 121 and relatively short lower linear segment 122, which are connected with an arched segment 123 which is convex leftward. The first annular member element 11 and the second annular member element 12 are connected between the upper linear segment of one annular member element and the lower linear segment of the other annular member element, i.e., 111 and 122, 121 and 112 with the connecting segments 15, 15. Taking into account of deformation the of stent at the time of expansion, that the connecting segment 15 is preferably formed into a pattern that smoothly connects the first annular member element 11 and the second annular member element 12. That is, the connecting segment is preferably formed into a pattern that provides the connection between annular member element 11 and second annular member element 12 with a curve profile which is free from angulated portion at least.

The adjoining two annular members 1, 1 are out of phase with each other so that the respective first annular member elements 11 and second annular member elements 12 of the annular members face each other (i.e., the junctions 18, 19 are disposed in the same straight lines parallel to the longitudinal axis of the stent), and the adjoining two annular members 1, 1 are coupled between the junctions 18, 19 of the connecting segments 15 and the upper linear segments 121, 111 of the respective annular members with the coupling elements 2.

The stent of this embodiment is excellent in flexibility for bending, and thus it is excellent in trackability to lumens as with that of embodiment 1. Further, the stent has good radial expandability, makes it easy to provide a lateral hole, and shows good structural balance at the time of expansion. In addition, the stent hardly produces shortening of the length since the adjoining two annular members are connected between the junctions which connect the connecting segments and the upper linear segments of the respective annular members.

Embodiment 4

Figure 8:
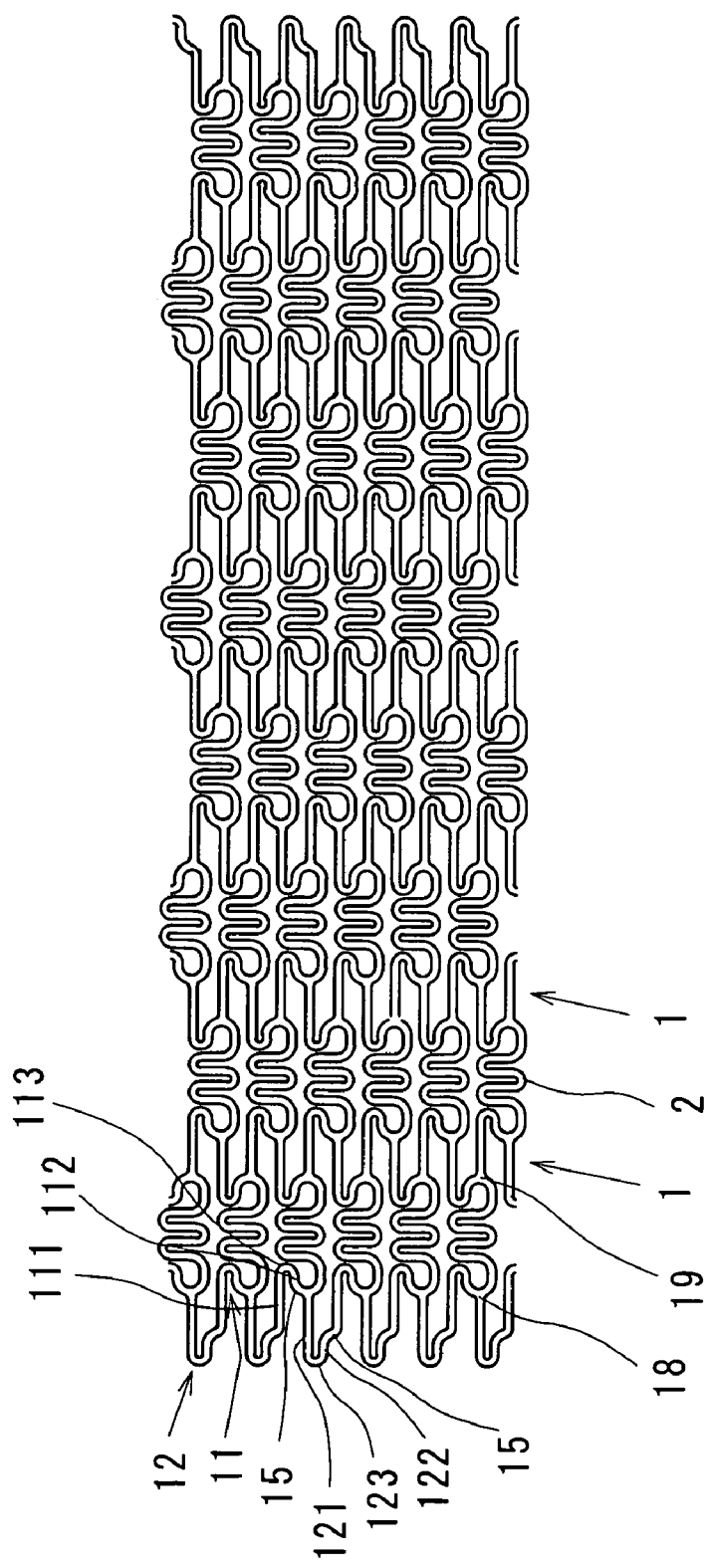
FIG. 8 is a development of a stent according to another embodiment of the present invention.

Embodiment 4 of the present invention will be demonstrated below, making reference to FIG. 8.

The stent of embodiment 4 is a modification of the stent of embodiment 3, in which the number of annular members 1 is set to 9 and the coupling elements are formed into a pattern as illustrated in FIG. 5D. As illustrated in FIG. 8, the stent comprises nine radially expandable annular members 1 which are arranged in the longitudinal direction of the stent. The adjoining two annular members 1, 1 are longitudinally connected with six coupling elements 2 of a pattern shown in FIG. 5D. The adjoining two annular members 1, 1 are coupled between junctions 18, 19 which connect respective connecting segment 15 and the upper linear segments 121, 111 with the coupling elements 2.

The stent of this embodiment is superior to that of embodiment 1 in flexibility for bending, and thus it is excellent in trackability to lumens. As with the stent of embodiment 1, the stent hardly produces shortening of the length, and has good radial expandability, makes it easy to provide a lateral hole, and shows good structural balance at the time of expansion.

Embodiment 5

Figure 10:
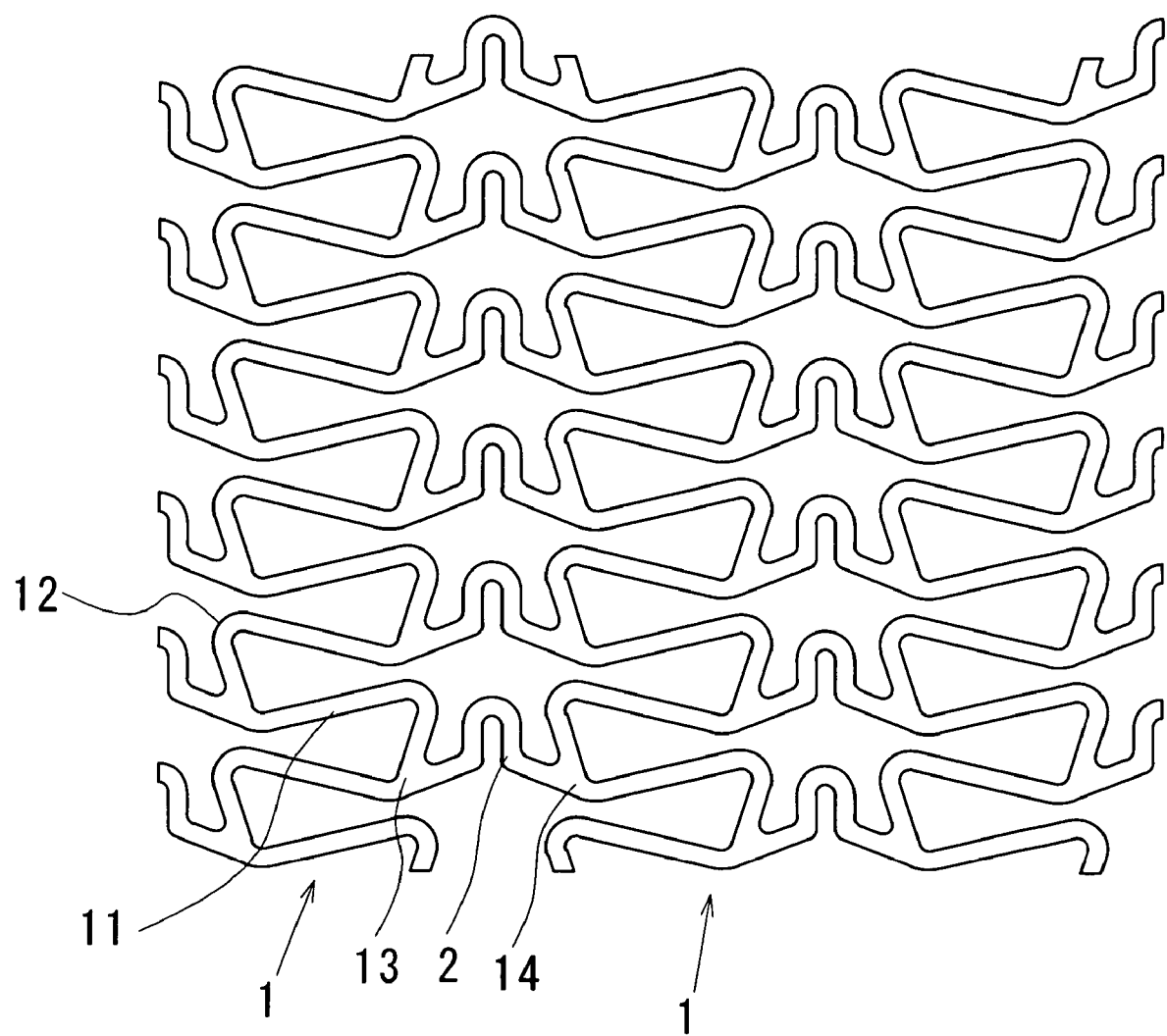
FIG. 10 is a partially enlarged view of FIG. 9.
Figure 11:
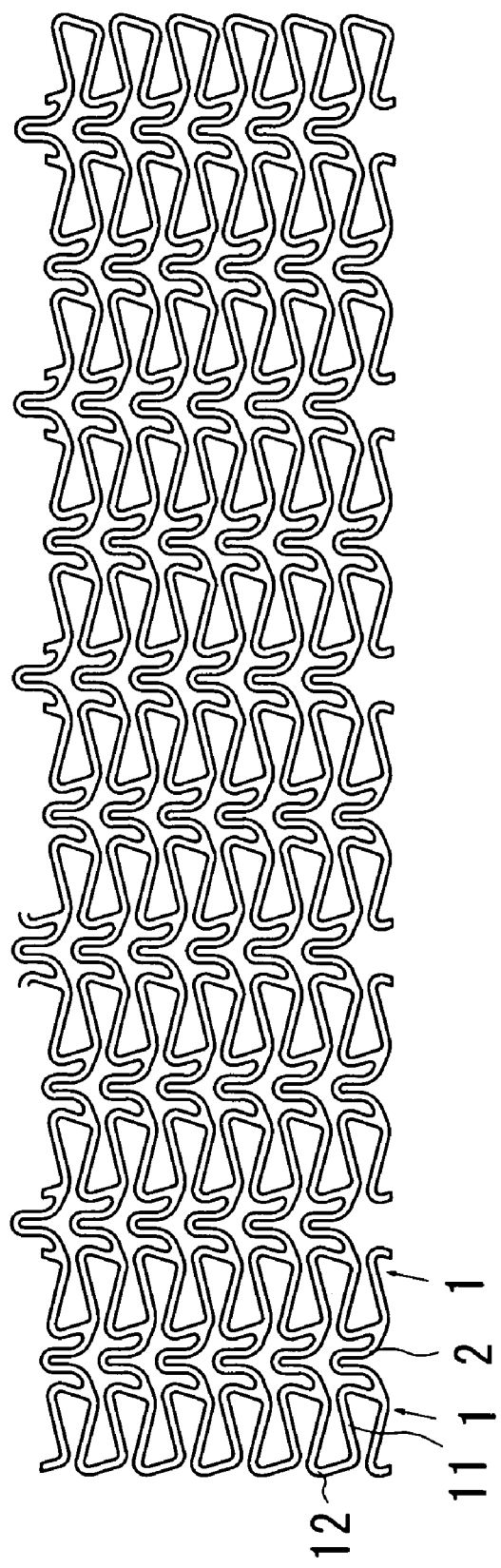
FIG. 11 is a development of a stent according to another embodiment of the present invention.

Embodiment 5 of the present invention will be demonstrated below, making reference to FIGS. 10 and 11.

The stent of embodiment 5 is a modification of the stent of embodiment 1, in which the first annular member elements 11 and the second annular member elements 12 are directly connected to each other. As illustrated in FIG. 10, the stent includes eleven radially expandable annular members 1 which are arranged in the longitudinal direction of the stent, and the adjoining two annular members 1, 1 are longitudinally connected with six coupling elements 2 of a pattern shown in FIG. 5A. The adjoining two annular members 1, 1 are coupled between respective junctions 13, 14 of the first annular member elements 11 and the second annular member elements 12.

Under the condition that the stent is unfolded onto a plane, the first annular member elements 11 and second annular member elements 12 are upwardly inclined to the longitudinal axis of the stent. The vertically-adjoining first annular member element 11 and second annular member element 12 are connected at the junction 13 when the first annular member element 11 is located above the second annular member element 12, or at the junction 14 when the first annular member element 11 is located below the second annular member element 12, as illustrated in FIG. 11. Under the condition that the stent is unfolded onto a plane, the adjoining annular members 1, 1 are oriented toward the same vertical direction. The adjoining two annular members 1, 1 are coupled between the junctions 14 of the right annular member 1 and the junctions 13 of the left annular member 1 with the coupling elements 2. It is preferred that the adjoining annular members 1, 1 are oriented toward the same vertical direction under the condition that the stent is unfolded onto a plane.

The stent of this embodiment has good flexibility for bending, and thus excellent in trackability to lumens as with that of embodiment 1. Further, the stent hardly produces shortening of the length.

Embodiment 6

Embodiment 6 of the present invention will be demonstrated below, making reference to FIG. 11.

The stent of embodiment 6 is a modification of the stent of embodiment 5, in which the coupling elements are formed into a pattern as illustrated in FIG. 5B. As illustrated in FIG. 11, the stent includes eleven radially expandable annular members 1 which are arranged in the longitudinal direction of the stent and the adjoining two annular members 1, 1 are longitudinally connected with six coupling elements 2 of a pattern shown in FIG. 5B. The adjoining two annular members 1, 1 are coupled between respective junctions 13, 14 with the coupling elements 2.

The stent of this embodiment is superior to that of embodiment 5 in flexibility for bending, and thus it is excellent in trackability to lumens. As with the stent of embodiment 1, the stent hardly produces shortening of the length, and has good radial expandability, makes it easy to provide a lateral hole, and shows good structural balance at the time of expansion.

[Tests for Flexibility, Shortening and Vessel Diameter-holding Capacity]

Figure 13:
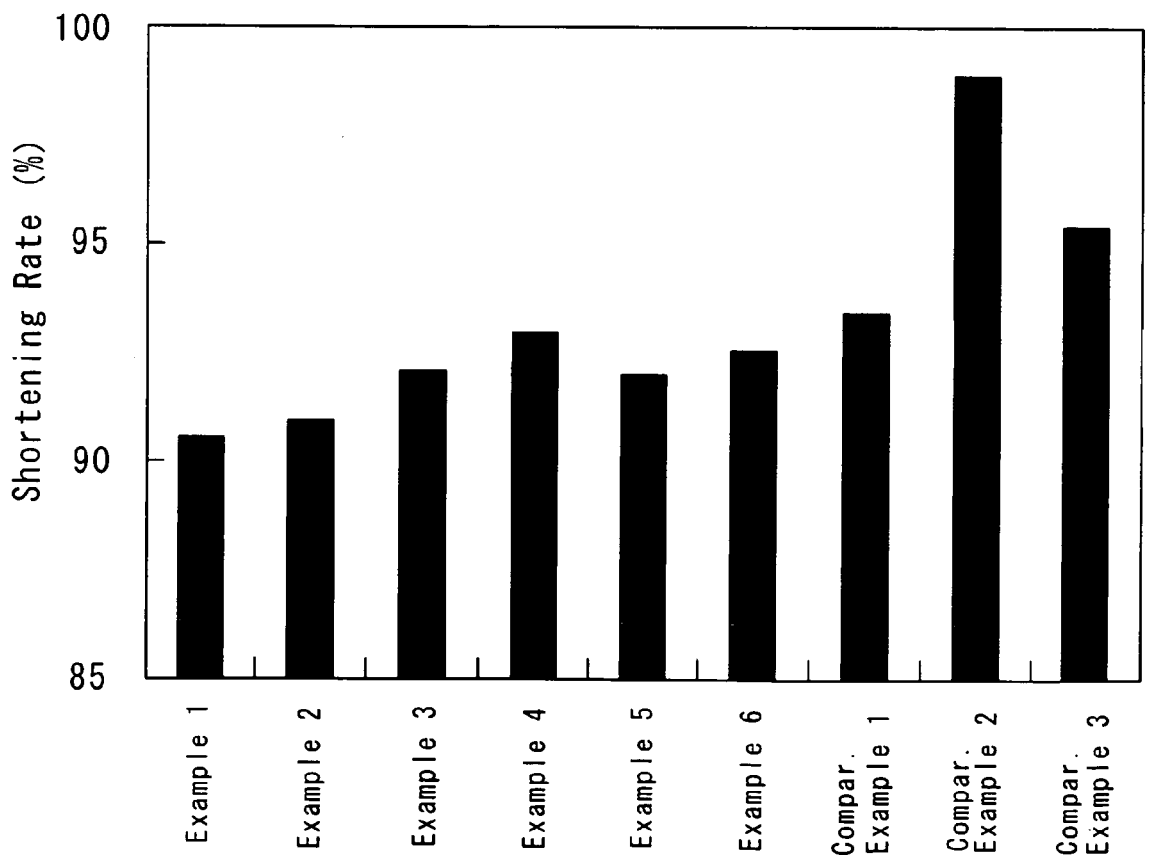
FIG. 13 is a diagram illustrating shortening comparison between the stent of the present invention and that of the prior art.
Figure 14:
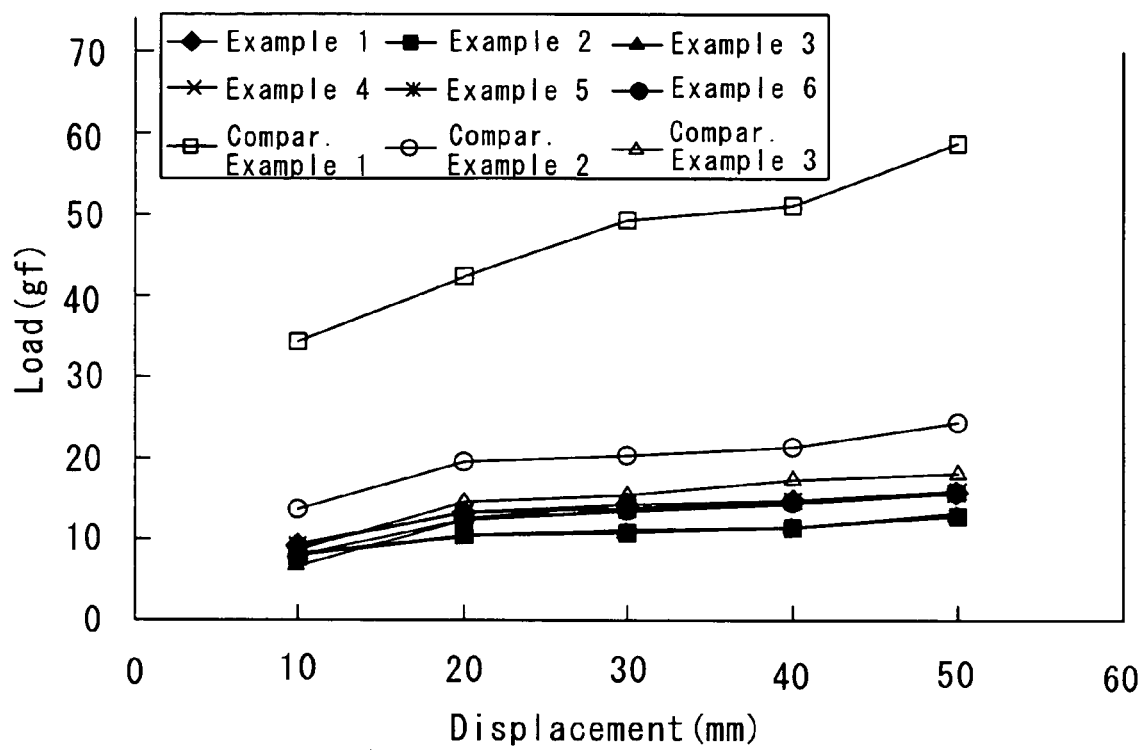
FIG. 14 is a diagram illustrating comparisons of vessel diameter-holding capacity between the stent of the present invention and that of the prior art.

For the stents each having the development as shown in Table 1, comparison was made on bendability (flexibility), shortening and vessel diameter-holding capacity. There were obtained results shown in FIGS. 12-14.

Figure 12:
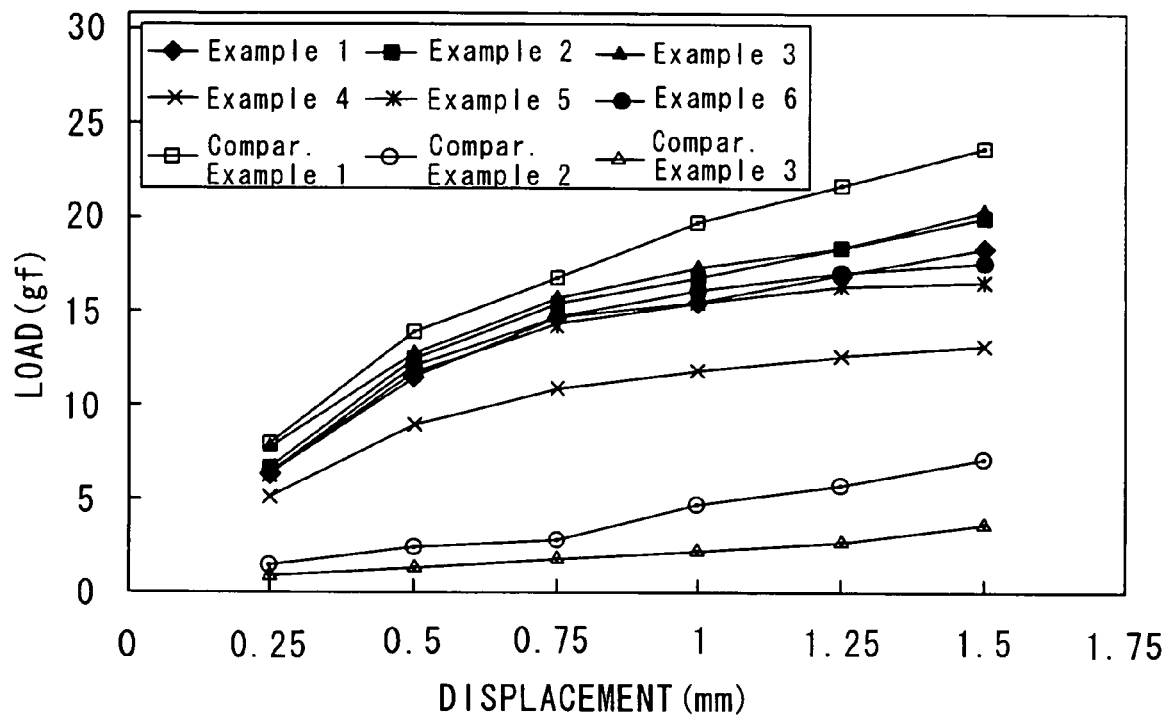
FIG. 12 is a diagram illustrating flexibility comparison between the stent of the present invention and that of the prior art.

From the results shown in FIG. 12, the stent of the present invention possesses flexibility superior to the stent of the prior art. From the results shown in FIGS. 13 and 14, it will be seen that the stent of the present invention possesses shortening and vessel diameter-holding capacity which are substantially equal to the stent of the prior art.

The measurement of flexibility was carried out by fixing the stent at one end and pushing a part of the stent 5 mm remote from the fixed point to bend the stent, and measuring a load which corresponds to the displacement magnitude.

The measurement of shortening was carried out by expanding the stent with a balloon of a 3.0 mm diameter at a pressure of 8 atm. (for comparative stents, at the recommended pressure) for 30 seconds, and then determining a length of the expanded stent with a profile projector (made by Mitutoyo Corporation).

The vessel diameter holding capacity was determined by expanding the stent with a balloon of a 3.0 mm diameter at a pressure of 8 atm. (for comparative stents, at the recommended pressure) for 30 seconds, and carrying out the compression test of the expanded stent with Autograph (made by Shimadzu Corporation). The vessel diameter holding capacity was determined by dividing the resultant data by the number of the annular members.

TABLE 1

Figure 9:
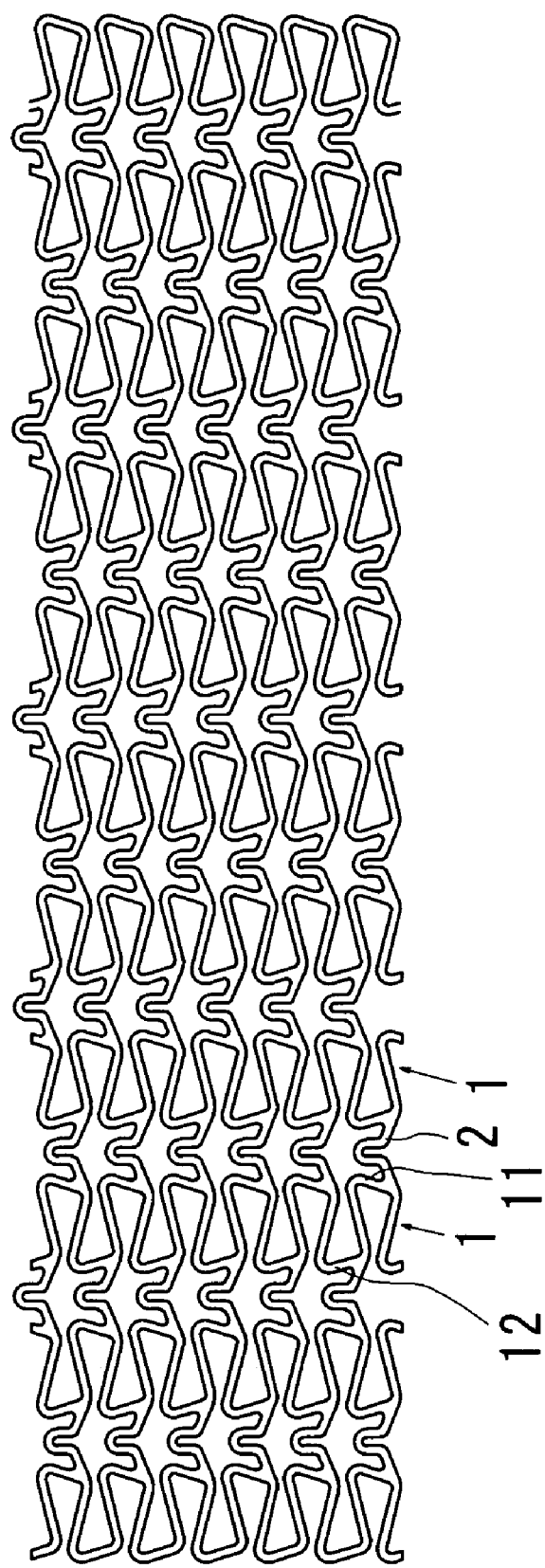
FIG. 9 is a development of a stent according to another embodiment of the present invention.
Figure 15:
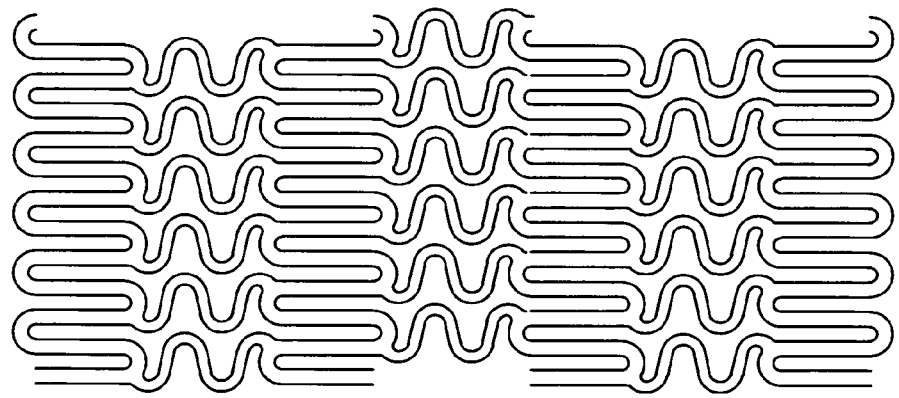
FIG. 15 is a development of a stent of the prior art.
Figure 16:
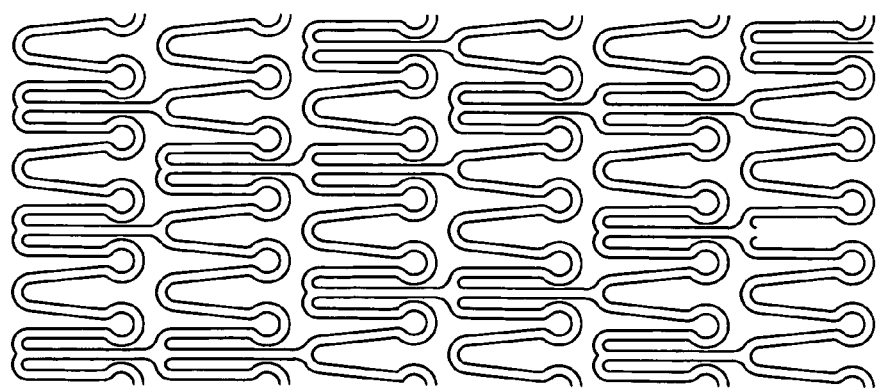
FIG. 16 is a development of another stent of the prior art.
Figure 17:
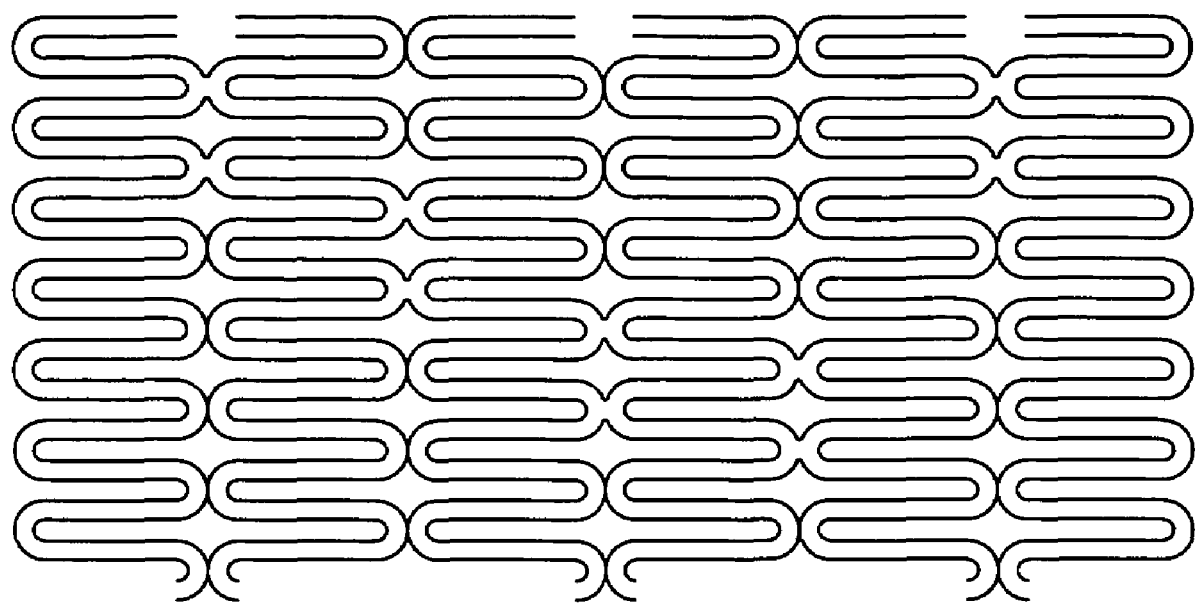
FIG. 17 is a development of still another stent of the prior art.

| | Remarks |
|---|---|
| Example 1 | FIG. 2(First and second annular member elements are connected with coupling elements and opposed on the same axis, the adjoining annular members are oriented toward the same direction, the number of annular members: 11, coupling element: FIG. 5A) |
| Example 2 | FIG. 6(coupling element: FIG. 5B, others are the same that of embodiment 1) |
| Example 3 | FIG. 7(adjoining annular members are oriented parallel to the longitudinal axis, the number of annular members: 12, coupling element: FIG. 5C, others are the same as that of embodiment 1) |
| Example 4 | FIG. 8(coupling element: FIG. 5A, the number of annular members: 9, coupling element: FIG. 5D, others are the same as that of embodiment 3) |
| Example 5 | FIG. 9(First and second annular member elements are connected directly, the adjoining annular members have the same orientation, the adjoining annular member elements are opposed on the same axis, the number of annular members: 11, coupling element: FIG. 5A) |
| Example 6 | FIG. 11(coupling element: FIG. 5B, others are the same as that of embodiment 4.) |
| Comparative Example 1 | FIG. 15(blood vessel-retaining portions of wavelike patterns and waved joint elements) |
| Comparative Example 2 | FIG. 16(blood vessel-retaining portions of a wavelike pattern are connected at the tops and bottoms of the waves) |
| Comparative Example 3 | FIG. 17(blood vessel-retaining portions with a wavelike pattern are connected at the tops of the waves.) |

The invention claimed is:

1. A flexible stent with good trackability to blood vessels, comprising radially expandable annular members which are aligned in a longitudinal direction of the stent, and one or more coupling elements that couple adjoining two annular members in the longitudinal direction of the stent, wherein said annular member comprises first annular member elements and second annular member elements, which have a plane symmetrical pattern and are alternately connected in the circumferential direction of the annular member, wherein, under the condition that the stent is unfolded onto a plane, said first annular member element includes one wave mountain, while said second annular member element includes one wave trough, the adjoining two annular members being connected between the respective junctions which connect the first annular member elements and second annular member elements, wherein the first annular member element and second annular member element are connected with connecting segments in the circumferential direction of the annular member, wherein, under the condition that the stent is unfolded onto a plane, the first annular member element includes a relatively long upper linear segment and a relatively short lower linear segment which are parallel to the longitudinal axis of the stent, said upper linear segment and lower linear segment being connected with an arched segment that is convex rightward, wherein said second annular member element includes a relatively long upper linear segment and a relatively short lower linear segment which are parallel to the longitudinal axis of the stent, said upper linear segment and lower linear segment being connected by an arched segment that is convex leftward, wherein the first annular member element and second annular member element are joined between the upper linear segment of one annular member element and the lower linear segment of the other annular member element, and wherein the adjoining two annular members are connected between the junctions having a pattern which is convex toward the annular member to be connected, among the respective junctions between the connecting segment and the upper linear segment or lower linear segment.

2. The stent according to claim 1, wherein the adjoining annular members are connected between the junctions which connect the respective connecting segments and upper linear segments.

3. The stent according to claim 1, wherein the adjoining annular members are connected between the junctions which connect the respective connecting segments and lower linear segments.

4. The stent according claim 1, wherein the adjoining annular members are out of phase with each other so that the first annular member elements and the second annular member elements of the respective annular members are opposed to each other on the same longitudinal lines.

5. The stent according claim 1, wherein the connecting segments are in the form of a linear line.

6. The stent according claim 1, wherein the connecting segments are in the form of a curved line.

7. The stent according to claim 6, wherein the curved line is a waveform.

8. The stent according to claim 7, wherein the curved line has a wave mountain.

9. The stent according to claim 7, wherein the curved line has plural wave mountains.

10. The stent according to claim 6, wherein the curved line is of an S-shaped or inverted S-shaped.

* * * * *